United States Patent [19]

Ribaldone et al.

[11] 3,960,866

[45] June 1, 1976

[54] PROCESS FOR PREPARING 1-AZA-2-HYDROXYBENZANTHRONE

[75] Inventors: Giuseppe Ribaldone, Gallarate; Giampiero Borsotti, Novara; Franco Gonzati, Saronno, all of Italy

[73] Assignees: Montedison S.p.A.; Aziende Colori Nazionali Affini ACNA S.p.A., both of Milan, Italy

[22] Filed: July 17, 1974

[21] Appl. No.: 489,351

[30] Foreign Application Priority Data

July 18, 1973   Italy .................................. 26722/73

[52] U.S. Cl. ............................... 260/278; 260/155; 260/272

[51] Int. Cl.² ........................................ C07D 217/24
[58] Field of Search ............................ 260/278, 272

[56]   References Cited
OTHER PUBLICATIONS

Boffa et al., Chem. Abstracts, 74:99877d (1971).

*Primary Examiner*—R. Gallagher

[57]   ABSTRACT

1-aza-2-hydroxybenzanthrone, useful as an intermediate for synthesizing dyes is obtained by the direct reaction of alkyl esters of anthraquinone-1-acetic acid with ammonia in hydroxylated solvents and in the presence of strong bases and/or reducing substances.

5 Claims, No Drawings

PROCESS FOR PREPARING 1-AZA-2-HYDROXYBENZANTHRONE

THE PRIOR ART

Italian Pat. No. 860,016 discloses a process for preparing 1-aza-2-hydroxybenzanthrone which involves reacting 1-(1,4,4a-tetrahydroanthraquinone)- methyl acetate with ammonia and subsequent dehydrogenation and cyclization in the presence of air and KOH:

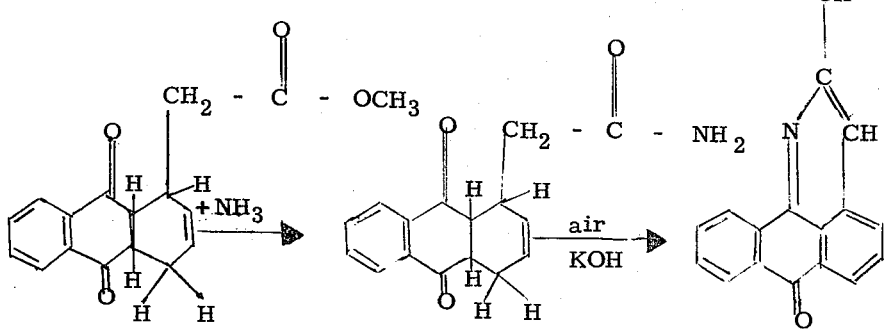

THE PRESENT INVENTION

The present invention provides a process for preparing 1-aza-2-hydroxybenzanthrone which is simpler and more economical than the previously known process.

According to this invention, 1-aza-2-hydroxybenzanthrone is obtained by direct reaction between alkyl esters of anthroquinone-1-acetic acid and ammonia in hydroxylated solvents and in the presence of strong bases and/or reducing agents, according to the following scheme:

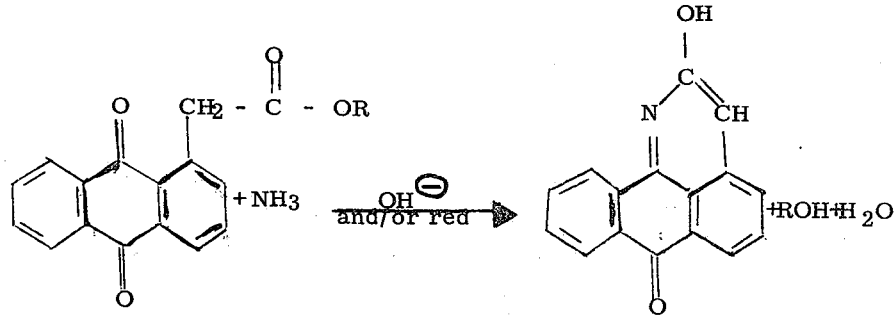

wherein: $R = C_1 - C_5$ alkyl-radical, and "red" means reducing agents.

In the absence of strong bases and/or of reducing substances, there is practically no reaction between alkyl-anthraquinone acetate and ammonia at temperatures below 35°C, while at temperatures above 35°C only small quantities of 1-aza-2-hydroxybenzanthrone are formed, along with some brown and violet products of unknown composition.

In the process of this invention, a strong excess of ammonia with respect to the ester, i.e., 10–50 moles of ammonia per 1 mole of ester, and preferably from 15 to 40 moles of ammonia to 1 mole of the ester, is used.

The strong base, for instance:

Na OH, KOH, Ba(OH)$_2$, Na$_2$O, CH$_3$ONa, CH$_3$OK, is used in at least the stoichiometric amounts with respect to the ester, and may be used in greater amounts such as, for instance, 1.5 equivalents of base per 1 mole of ester.

The reducing substances which are useful in the practice of this invention in catalytic amounts include sodium hydrosulphite, formaldehyde, sodium sulphoxylate (Rongalite), zinc, iron, aluminum and tin.

The hydroxylated reaction solvent used in the present process can be an aliphatic mono- or poly- hydroxylated alcohol containing from 1 to 10 carbon atoms. The useful solvents include methanol, ethanol, isobutyl alcohol and ethylene glycol. When reducing substances are present, water can be used as the reaction solvent.

The reaction can be carried out at a temperature of from room temperature (20°–30°C) to 80°C. Temperatures below room temperature and higher than 80°C are of scant practical interest in the process of this invention.

The reaction time which in general is from 3 to 20 hours can vary depending on the temperature, the quantity of ammonia used and on whether both reducing agents and strong bases are used, or one or the other is absent.

When strong bases are used in the absence of reducing agents, it is preferable to carry out the reaction at room temperature for 3 to 6 hours in an alcoholic medium. When strong bases and reducing agents are both present, the reaction medium can be aqueous or alcoholic.

Under the stated conditions, the ester of anthraquinone-acetic acid reacts with the NH$_3$ to form, directly, the 1-aza-2-hydroxybenzanthrone, without the necessity of isolating the intermediate product 1-anthraquinone acetamide.

The presence of both reducing substances and strong bases, in addition to permitting the use of water as the reaction medium, also results in a considerable increase in the speed of the reaction.

In general, in practicing the embodiment of the invention in which reducing agents are absent, there is first prepared a solution or suspension of the strong base in mono- or poly- hydroxylated aliphatic alcohols, the solution of suspension is treated with gaseous ammonia under cooling and until the desired amount of $NH_3$ is absorbed, after which the ester of anthraquinone-1-acetic acid is added. The ester remains prevailingly in suspension due to its low solubility in hydroxylated organic solvents.

The mixture thus prepared is stirred continuously at 25°–30°C in a pressure-tight vessel (e.g., an autoclave) until the ester disappears.

On completion of the reaction, the mixture is either practically homogeneous and has a red-violet color, or it is heterogeneous, especially when the strong base is barium oxide or hydroxide. This is because the barium salt of 1-aza-2-hydroxybenzanthrone is only poorly soluble in hydroxylated organic solvents.

If the strong base salt of the 1-aza-2-hydroxybenzanthrone is in solution, the solution is freed of the excess $NH_3$, possibly under vacuum or by bubbling a stream of an inert gas through the solution. The solution is then diluted with $H_2O$, filtered to remove any solid substances and acidified. The red 1-aza-2-hydroxybenzanthrone which is thus precipitated is filtered off, washed with $H_2O$, and dried. The dried product is yellow.

Before diluting the solution with $H_2O$, it is possible to recover the solvent by distillation under vacuum at a temperature which is kept at 40°C or lower (to avoid alteration of the reaction product). The solvent may also be recovered by adding ethyl ether to the solution to precipitate the 1-aza-2-hydroxybenzanthrone which is filtered off and dissolved in $H_2O$, while the solution is then acidified.

The same procedure can be used when the strong base employed is BaO or $Ba(OH)_2$. In that case the violet-colored Ba salt of 1-aza-2-hydroxybenzanthrone is filtered off, suspended in $H_2O$, and the suspension is acidified, for instance by the addition of concentrated HCl.

The procedure described can also be used in carrying out the embodiment of the invention in which both strong bases and reducing agents are used. However, in that event, the solvent may be water or a monohydric or polyhydric alcohol.

In carrying out the embodiment in which reducing substances are used but strong bases are absent, it is preferable to carry out the reaction at higher temperatures (50° to 70°C for 3 to 6 hours) or at room temperature but for longer reaction times, for instance a reaction time of from 15 to 20 hours. Under such conditions, the 1-aza-2-hydroxybenzanthrone is still obtained directly, whereas when the reducing agents are used but strong bases are absent, if the reaction is carried out at room temperature for short times, the reaction product will consist essentially of 1-aza-2hydroxy-benzanthrone plus some anthraquinone 1-acetic acid amide which, by subsequent treatment with a strong base can be cyclized to 1-aza-2-hydroxybenzanthrone.

In a presently preferred embodiment of the invention, the reaction is carried out in an autoclave in the presence of reducing substances and in the absence of strong bases, at temperatures of from 50° to 70°C for a reaction time of from 5 to 10 hours, to obtain a suspension of a reaction product consisting of 1-aza-2-hydroxybenzanthrone.

In said presently preferred embodiment, the ester of anthraquinone-1-acetic acid and a catalytic quantity of the reducing substance are added to a solution of $NH_3$ in the hydroxylated solvent which may be a hydroxylated organic solvent or water. The resulting mixture is stirred at 50° to 70°C for a reaction time of 3 to 10 hours which can vary with the ester used, the reaction temperature, and the concentration of the $NH_3$.

On completion of the reaction, the reaction mixture consists essentially of a 1-aza-2-hydroxybenzanthrone suspension which is treated with an aqueous solution of NaOH to solubilize the aza-hydroxybenzanthrone. Thereafter, the solution is worked up as described hereinabove.

The following examples are given to illustrate the invention and are not intended to be limiting.

EXAMPLE 1

A solution of 0.8 g of 97% NaOH in 30 cc of methanol, cooled down to −10°C, was made to absorb 5 g of $NH_3$; thereupon there were added 5 g of methyl anthraquinone-1-acetate (having a titer of 97.5%).

The mixture was kept under stirring for 6 hours at room temperature and under a pressure of 1.4 ata. At the end of the reaction the mixture appeared completely homogeneous and of a red-violet hue. It was diluted with water at 60°C up to 200 cc, filtered on diatomite and acidified with concentrated HCl. A red-colored precipitate was obtained. It was filtered, washed with water until neutral, and finally dried at 130°C until it attained a constant weight. 3.9 g of 1-aza-2-hydroxybenzanthrone in the pure state were obtained as a yellow powder, corresponding to a 90.6% yield.

The elementary analysis and the IR-spectrum confirmed the structure of the compound.

EXAMPLE 2

By 300 cc of methanol, cooled down to −10°C, there were absorbed 60 g of $NH_3$. Thereupon 50 g of methyl anthraquinone-1-acetate (with a titer of 96.5%) and 1 g of commercial sodium hydrosulphite (titer 85%) were added. This mixture was kept under stirring at 25°C and under a pressure of 1.4 ata. After 2.5 hours the red-brown colored mixture suddenly became thicker. The stirring was carried on for another 2 hours. The mixture was then poured into water at 60°C, additioned with 10 g of NaOH dissolved in water (total volume: 2 liters), heated at 60° − 70°C for 20 minutes and finally the solution was filtered on diatomite.

The filtrate, heated at 50° − 60°C, was then acidified with concentrated HCl. The red precipitate was filtered and dried at 130°C until it reached a constant weight. 40.0 g of pure 1-aza-2-hydroxybenzanthrone were obtained, corresponding to a yield of 93.8%.

EXAMPLE 3

200 cc of methanol, cooled down to −10°C, were made to absorb 40 g of $NH_3$, whereupon there were added 40 g of ethyl anthraquinone-1-acetate (with a titer of 90%) and 0.5 g of zinc powder. This mixture was kept under stirring for 5 hours at room temperature and under a pressure of 1.4 ata. At the end of the reaction, the ammonia and the methanol were removed from the red-brown reaction mixture operating under vacuum at 40°C in a thin layer evaporator.

The residue was treated with 6 g of NaOH dissolved in 2 liters of water, then heated for 20 minutes at 60° – 70°C. The solution was than filtered on diatomite and the filtrate, heated to 60°C, was acidified with concentrated HCl. The red precipitate thus obtained was filtered and dried at 130°C until it reached a constant weight. Thereby were obtained 27.2 g of pure 1-aza-2-hydroxybenzanthrone corresponding to a yield of 90%.

EXAMPLE 4

A suspension of 50 g of methyl anthraquinone-1-acetate (having a titer of 96.5%) and of 0.5 g of zinc powder in 500 cc of a concentrated aqueous ammonia solution (titer of 28% $NH_3$) was kept under stirring at room temperature and under atmospheric pressure for 5 hours, in a closed vessel so as to avoid losses of $NH_3$. At the end of the reaction there was obtained a red-brown colored suspension that was poured into 1300 cc of an aqueous solution of NaOH containing 10 g of NaOH. This mixture was heated for 20 minutes at 70°C and the solution thus obtained was filtered on diatomite. The filtrate, heated at 60°C, was acidified with concentrated HCl. The red precipitate obtained was then filtered and dried at 130°C until it reached a constant weight. Thereby were obtained 39.4 g of pure 1-aza-2-hydroxybenzanthrone, corresponding to a yield of 92.5%.

EXAMPLE 5

A suspension of 35 g of methyl anthraquinone-1-acetate (titer: 96.5%) and of 0.35 g of zinc powder in 320 cc of a concentrated aqueous solution of ammonia (titer: 28% of $NH_3$), was maintained under stirring for 5 hours in an autoclave at 70C and at a pressure of about 3 ata. At the end of the reaction there was obtained a red-brown suspension of a product consisting of aza-hydroxybenzanthrone which was poured into 750 cc of an aqueous solution of NaOH containing 9 g of NaOH, in order to solubilize the aza-hydroxybenzanthrone.

The suspension was then filtered at 30°C on diatomite in order to eliminate the existing solid impurities. This filtrate was acidified at 30°C to a pH = 6 with concentrated HCl. The red precipitate obtained was filtered and then dried at 110°C until its weight remained constant. Thereby were obtained 26.9 g of pure 1-aza-2-hydroxybenzanthrone, corresponding to a yield of about 91%.

The 1-aza-2-hydroxybenzanthrone is a useful intermediate in the synthesis of dyes. For instance, it is an excellent intermediate in the synthesis of azo-dyes. Thus, when the 1-aza-2-hydroxybenzanthrone is coupled with a diazo of p-nitroaniline by conventional techniques, there is obtained a brick-red dye of the formula:

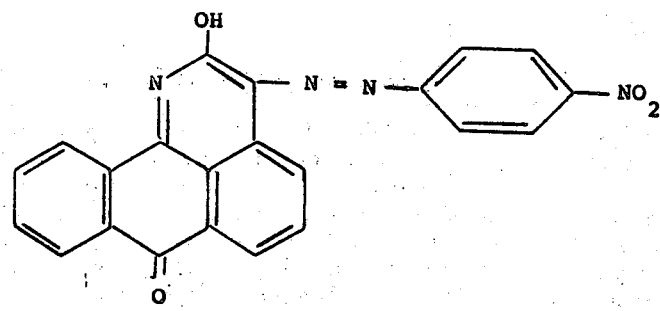

The 1-aza-2-hydroxybenzanthrone is also useful as intermediate in the synthesis of excellent vat dyes. For instance when it is used in the processes described in Italian Patents Nos. 869,961 and 901,929, excellent vat dyes are obtained which range from bright blue to violet blue in color and belong to the iso-violanthrone series of dyestuffs.

The processes of the Italian Patents Nos. 869,961 and 901,929 involve reacting 1-aza-2-hydroxybenzanthrone with bromine and alkylation of the bromine-derivative to the bromo-alkoxy-derivative, which in turn is sulphurated.

The thiobis-(aza-alkoxy-benzanthrone) is finally subjected to alkaline condensation thus obtaining blue vat dyes of the formula:

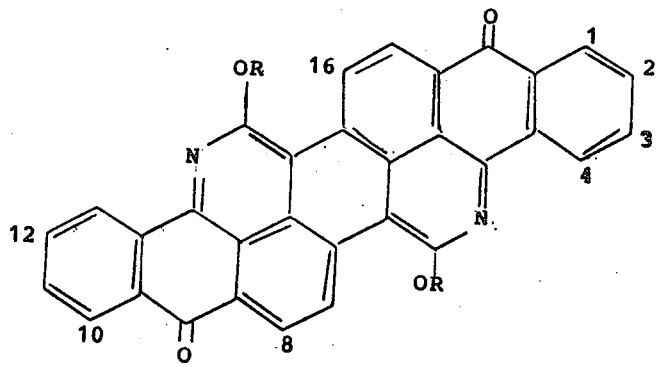

6,15-dialkoxy-5,14-diaza-isoviolanthrone
6,15-dialkoxy-5,14-diaza-dinaphto[1.2.3-cd; 1'.2'.-3'.-lm] perylene-9.18-dione.

In the formula the radical R represents a linear or branched alkyl, containing from 1 to 4 carbon atoms.

We claim:
1. Process for preparing 1-aza-2-hydroxybenzanthrone, comprising reacting an ester of anthraquinone-1-acetic acid with ammonia in a hydroxylated solvent and in the presence of at least the stoichiometric amount of a strong base and/or of a catalytic amount of a reducing substance, according to the scheme:

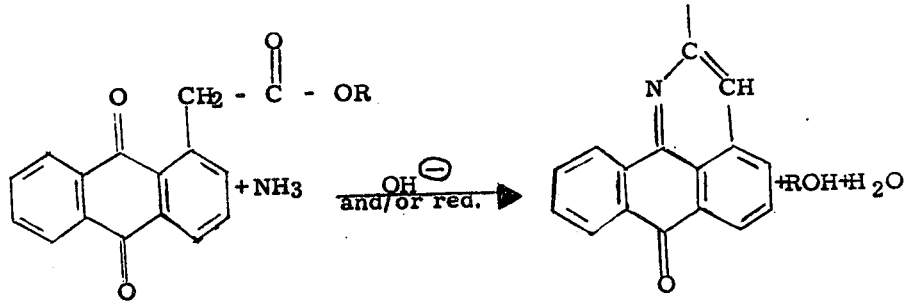

wherein: R = Cl –C$_5$ alkyl, and "red." means reducing agent,
the hydroxylated solvent being selected from the group consisting of water, methanol, ethanol, isobutanol and ethylene glycol; the strong base being selected from the group consisting of NAOH, KOH, Ba(OH)$_2$, Na$_2$O, CH$_3$ONa, and CH$_3$OK; the reducing substance being selected from the group consisting of sodium hydrosulphite, formaldehyde, sodium sulphoxylate, zinc, iron, aluminum and tin; and the reaction being carried out at a temperature comprised between 20° and 80°C.

2. The process of claim 1, in which the reaction is carried out in methanol in the presence of NaOH.

3. The process of claim 1, in which the reaction is carried out in methanol in the presence of sodium hydrosulphite.

4. The process of claim 1, in which the reaction is carried out in methanol in the presence of zinc powder.

5. Process according to claim 1, in which the reaction is carried out in water at temperatures comprised between 50° and 70°C, in the presence of catalytic quantities of reducing substances and in the absence of strong bases.

* * * * *

UNITED STATES PATENT OFFICE
CERTIFICATE OF CORRECTION

Patent No. 3,960,866                     Dated June 1, 1976

Inventor(s)  Giusepee Ribaldone et al.

It is certified that error appears in the above-identified patent and that said Letters Patent are hereby corrected as shown below:

Col. 3, line 7,    after "solution" the word "of" should be

- - - or - - -.

Claim 1, first line after the schematic showing:

"R=C1-$C_5$ alkyl"   should be

- - - R=$C_1$-$C_5$ alkyl - - -.

Signed and Sealed this

Eighteenth Day of April 1978

[SEAL]

Attest:

RUTH C. MASON
Attesting Officer

LUTRELLE F. PARKER
Acting Commissioner of Patents and Trademarks